Figure 1:
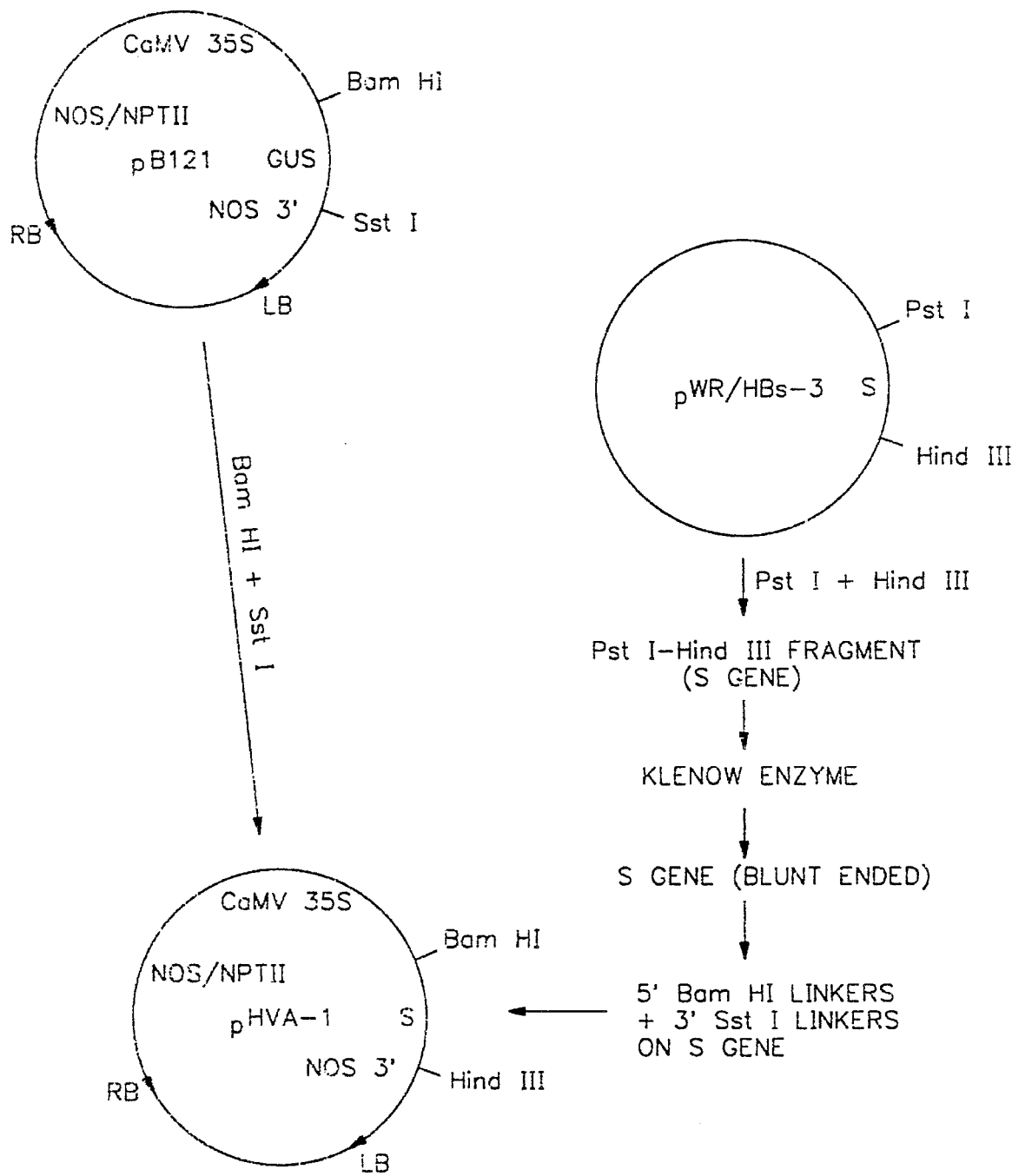
Figure 2:
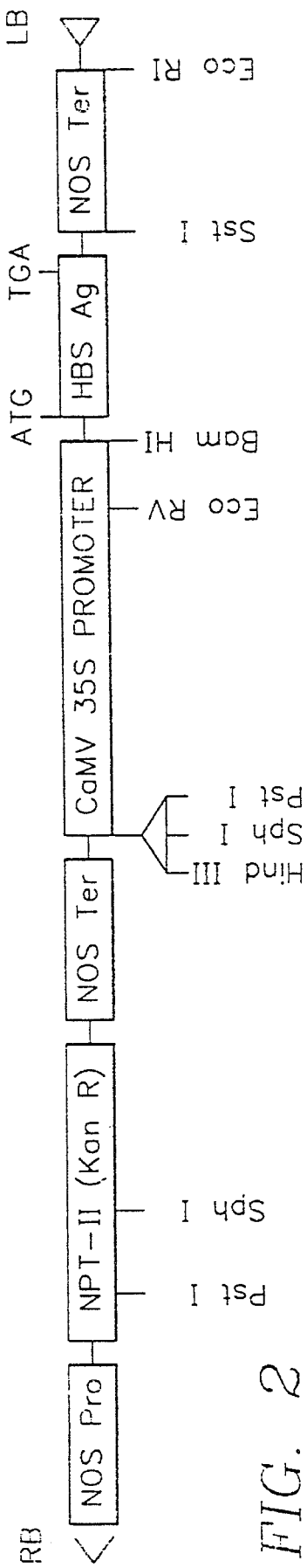

United States Patent [19]

Lam et al.

[11] Patent Number: 5,484,719
[45] Date of Patent: Jan. 16, 1996

[54] VACCINES PRODUCED AND ADMINISTERED THROUGH EDIBLE PLANTS

[75] Inventors: Dominic M. Lam, The Woodlands; Charles J. Arntzen, College Station, both of Tex.

[73] Assignee: Edible Vaccines, Inc., Conroe, Tex.

[21] Appl. No.: 156,508

[22] Filed: Nov. 23, 1993

Related U.S. Application Data

[63] Continuation of Ser. No. 750,049, Aug. 26, 1991, abandoned.

[51] Int. Cl.$^6$ .......................... C12N 15/00; C12N 15/36; C12N 15/82; A01H 5/00
[52] U.S. Cl. .................... 435/172.3; 435/320.1; 435/69.3; 800/205; 800/DIG. 43
[58] Field of Search .......................... 800/205, DIG. 43; 435/320.1, 69.3, 172.3; 424/88

[56] References Cited

U.S. PATENT DOCUMENTS

| | | | |
|---|---|---|---|
| 4,940,835 | 7/1990 | Shah et al. | 800/205 |
| 4,956,282 | 9/1990 | Goodman et al. | 435/69.51 |

FOREIGN PATENT DOCUMENTS

| | | | |
|---|---|---|---|
| 8700865 | 2/1987 | WIPO | C12P 21/00 |
| WO90/02484 | 3/1990 | WIPO | A01H 5/00 |
| 9010076 | 9/1990 | WIPO | C12N 15/82 |

OTHER PUBLICATIONS

Mason, Hugh S., Dominic Man–Kit Lam, and Charles Arntzen, "Expression of Hepatitis B Surface Antigen in Transgenic Plants", *Proc. Natl. Acad. Sci. USA*, vol. 89, pp. 11745–11749, (Dec. 1992).
Clontech Laboratories, Inc., Palo Alto, Calif., Product Catalog, p. 18.4, (1991).
Melnick, J. L., Bul. W.H.O. 67(2), 105–112 (1989).
Valenzuela, P. et al., Nature 298, 347–350 (1982).
Kupper, H. et al., Nature 289, 555–559 (1981).
Benfey, P. N. and Chua, N. H., Science 244, 174–181 (1989).
Horsch, R. B. et al., in Plant Molecular Biology Manual A5 (1988) pp. 1–9.
Rhodes, C. A. et al., Science 240, 204–207 (1988).
Toriyama, K. et al., Bio/Technology 6, 1072–1074 (1988).
Zhang, W. and Wu, R., Theor. Appl. Genet. 76, 835–840 (1988).
Wu, R. in Plant Biotechnology (1989) pp. 35–51.
Vaccination Strategies of Tropical Diseases, ed., Liew, F. Y. (1989) table of contents, only.
New Strategies in Parasitology, ed., McAdam, K. P. W. J. (1989) table of contents, only.
Murray, P. K., Vaccine 7, 291–299 (1989).
Weber, J. L. et al., Exp. Parasitology 63, 295–300 (1987).
Hoffman, S. L. et al., Science 252, 520–521 (1991).
Khusmith, S. et al., Science 252, 715–718 (1991).
Kaslow, D. C. et al., Science 252, 1310–1313 (1991).
Frasch, A. C. C. et al., Parasitology Today 7, 148–151 (1991).
Mitchell, G. F., Parasitology Today 5, 34–37 (1989).
Capron, A. et al., Science 238, 1065–1072 (1987).
Lanar, D. et al., Science 234, 593–596 (1986).
Deak, M. et al., Plant Cell Rep. 5, 97–100 (1986).
McCormick, S. et al., Plant Cell Rep. 5, 81–84 (1986).
Shahin, E. and Simpson, R., Hort. Sci. 21, 1199–1201 (1986).
Umbeck, P. et al., Bio/Technology 5, 263–266 (1987).
Christou, P. et al., Trends Biotechnol. 8, 145–151 (1990).
Datta, S. K. et al., Bio/Technology 8, 736–740 (1990).
Hinchee, M. A. W. et al., Bio/Technology 6, 915–922 (1988).
Raineri, D. M. et al., Bio/Technology 8, 33–38 (1990).
Fromm, M. E. et al., Bio/Technology 8, 833–839 (1990).
Gordon–Kamm, W. J. et al., The Plant Cell 2, 603–618 (1990).
Potrykus, I., Annu. Rev. Plant Physiol., Plant Mol. Biol. 42, 205–225 (1991).
Shimamoto, K. et al., Nature 338, 274–276 (1989).
Klee, H. J. et al., Annu. Rev. Plant Physiol. 38, 467–486 (1987).
Klee, H. J. and Rogers, S. G. in Cell Culture and Somatic Cell Genetics of Plants, vol. 6, Molecular Biology of Plant Nuclear Genes (1989) pp. 2–25.
Gatenby, A. A. in Plant Biotechnology (1989) pp. 93–112.
Paszkowski, J. et al. in Cell Culture and Somatic Cell Genetics of Plants, vol. 6, Molecular Biology of Plant Nuclear Genes (1989) pp. 52–68.
Klein, T. M. et al., in Progress in Plant Cellular and Molecular Biology (1988) pp. 56–66.
DeWet, J. M. J. et al., in Experimental Manipulation of Ovule Tissues (1985) pp. 197–209.
Zhang, H. M. et al., Plant Cell Rep. 7, 379–384 (1988).
Fromm, M. E. et al., Nature 319, 791–793 (1986).
Hess, D., Int. Rev. Cytol. 107, 367–395 (1987).
Klein, T. M. et al., Bio/Technology 6, 559–563 (1988).
McCabe, D. E. et al., Bio/Technology 6, 923–926 (1988).
Sanford, J. C., Physiol. Plant. 79, 206–209 (1990).

(List continued on next page.)

*Primary Examiner*—David T. Fox
*Assistant Examiner*—Charles Rories
*Attorney, Agent, or Firm*—C. Steven McDaniel; Conley, Rose & Tayon

[57] ABSTRACT

The oral vaccine of the present invention is produced in edible transgenic plants and then administered through the consumption of the edible portion of those plants. A DNA sequence encoding for the expression of a surface antigen of a pathogen is isolated and ligated to a promoter which can regulate the production of the surface antigen in a transgenic plant. This gene is then transferred to plant cells using a procedure that results in its integration into the plant genome, such as through the use of an *Agrobacterium tumenfaciens* plasmid vector system. Preferably, the foreign gene is expressed in an portion of the plant that is edible by humans or animals. The vaccine is administered through the consumption of the edible plant as food, preferably in the form of a fruit or vegetable juice which can be taken orally.

14 Claims, 2 Drawing Sheets

OTHER PUBLICATIONS

Neuhaus, G. et al., Theor. Appl. Genet. 75, 30–36 (1987).

Neuhaus, G. and Spangenberg, G., Physiol. Plant. 79, 213–217 (1990).

Ohta, Y. Proc. Nat'l. Acad. Sci. U.S.A. 83, 715–719 (1986).

Futterer, J. et al., Physiol. Plant. 79, 154–157 (1990).

Watson, J. D. et al., Recombinant DNA, a Short Course (1983) pp. 164–175.

White, F. F. in Plant Biotechnology (1989) pp. 3–34.

Fraley, R. T. in Plant Biotechnology (1989) pp. 395–407.

Elliston, K. and Messing, J. in Plant Biotechnology (1989) pp. 115–139.

Wenzler, H. C. et al., Plant Mol. Biol. 12, 41–50 (1989).

Weising, K. et al., Annu. Rev. Genet. 22, 421–477 (1988).

An, G., Meth. Enzymol. 153, 292–305 (1987).

Maniatis, T. et al., Molecular Cloning, A Laboratory Manual (1982) pp. 368–369.

Chang, A. et al., Proc. Nat'l. Acad. Sci., U.S.A. 86, 9611–9615 (1989).

Peng, Y. W. and Lam, D. M. K., Vis. Neurosci. 6, 357–370 (1991).

Persing, D. H. et al., Proc. Nat'l. Acad. Sci., U.S.A. 82, 3440–3444 (1985).

Pasek, M. et al., Nature 282, 575–579 (1979).

Cattaneo, R. et al., Nature 305, 336–338 (1983).

D. Ganem et al., Ann. Rev. Biochem, vol. 56, (1987) pp. 651–693.

L. Hoffman et al. Plant Mol. Biol., vol. 11 (1988) pp. 717–729.

H. Mason et al., PNAS, vol. '89 (1992) pp. 11745–11749.

B. Larkins et al. (abstract) J. Cell Biochem., Suppl. O (9 Part C) p. 264.

Schödel, F. et al., "Recombinant HBV Core Particles Carrying Immunodominant B–cell Epitopes of the HBV Pre–S2 Region," *Vaccines 90,* published by Cold Spring Harbor Laboratory Press (Cold Spring Harbor, N.Y.), F. Brown, et al., eds., pp. 193–198, (1990).

Melnick, J. L. "Virus Vaccines: Principles and Prospects," in *Bulletin of the World Health Organization,* vol. 67, No. 2, pp. 105–112 (1989).

de Aizpurua, H. J., et al., "Oral Vaccination, Identification of Classes of Proteins that Provoke an Immune Response Upon Oral Feeding," in *J. Exp. Med.,* vol. 167, pp. 440–451 (1988).

Valenzuela, P., et al., "Synthesis and Assmebly of Hepatitis B Virus Surface Antigen Particles in Yeast," in *Nature,* vol. 298, pp. 347–350 (1982).

Schödel, F., et al., "Expression of Hepatitis B Virus Core T–cell Epitopes and pre–S2 B–cell Epitope as Fusion Protein with LT–B in Salmonella for Oral Vaccination," in *Progress in Hepatitis B Immunization,* published by Colloque INSERM/John Libbey Eurotext Ltd., Coursaget, P., et al., eds., pp. 43–50 (1990).

Godet, M., et al., "Processing and Antigenicity of Entire and Anchor–Free Spike Glycoprotein S of Coronavirus TGEV Expressed by Recombinant Baculovirus," in *Virology,* vol. 185, pp. 732–740 (1991).

Schödel, F., et al., "Expressions of Hepatitis B Virus Antigens in Attenuated Salmonellae for Oral Immunization," in *Research in Microbiology* (Paris), vol. 141, pp. 831–837 (1990).

Richman, L. K., et al. Journal of Immunology, vol. 121 (1978) pp. 2429–2434.

Brisson, N., et al. Methods in Enzymology, vol. 118 (1986) pp. 659–668.

J. Salfeld et al. J. of Virology, vol. 63, #2 (1989) pp. 798–808.

D. Maskell et al. Vaccines '86, Cold Spring Harbor Lab, N.Y., 1986, pp. 213–217.

VACCINES PRODUCED AND ADMINISTERED THROUGH EDIBLE PLANTS

This is a continuation of application Ser. No. 07/750,049, filed on Aug. 26, 1991, now abandoned.

BACKGROUND OF THE INVENTION

This invention relates generally to oral vaccines and more particularly to the production of oral vaccines in edible transgenic plants and the administration of the oral vaccines through the consumption of the edible transgenic plants by humans and animals.

Diseases have been a plague on civilization for thousands of years, affecting not only man but animals. In economically advanced countries of the world, diseases are 1) temporarily disabling; 2) permanently disabling or crippling; or 3) fatal. In the lesser developed countries, diseases tend to fall into the latter two categories, permanently disabling or crippling and fatal, due to many factors, including a lack of preventative immunization and curative medicine.

Vaccines are administered to humans and animals to induce their immune systems to produce antibodies against viruses, bacteria, and other types of pathogenic organisms. In the economically advanced countries of the world, vaccines have brought many diseases under control. In particular, many viral diseases are now prevented due to the development of immunization programs. The virtual disappearance of smallpox, certainly, is an example of the effectiveness of a vaccine worldwide. But many vaccines for such diseases as poliomyelitis, measles, mumps, rabies, foot and mouth, and hepatitis B are still too expensive for the lesser developed countries to provide to their large human and animal populations. Lack of these preventative measures for animal populations can worsen the human condition by creating food shortages.

The lesser developed countries do not have the monetary funds to immunize their populations with currently available vaccines. There is not only the cost of producing the vaccine but the further cost of the professional administration of the vaccine. Also, some vaccines require multiple doses to maintain immunity. Therefore, often, the countries that need the vaccines the most can afford them the least.

Underlying the development of any vaccine is the ability to grow the disease causing agent in large quantities. At the present, vaccines are usually produced from killed or live attenuated pathogens. If the pathogen is a virus, large amounts of the virus must be grown in an animal host or cultured animal cells. If a live attenuated virus is utilized, it must be clearly proven to lack virulence while retaining the ability to establish infection and induce humoral and cellular immunity. If a killed virus is utilized, the vaccine must demonstrate the capacity of surviving antigens to induce immunization. Additionally, surface antigens, the major viral particles which induce immunity, may be isolated and administered to proffer immunity in lieu of utilizing live attenuated or killed viruses.

Vaccine manufacturers often employ complex technology entailing high costs for both the development and production of the vaccine. Concentration and purification of the vaccine is required, whether it is made from the whole bacteria, virus, other pathogenic organism or a sub-unit thereof. The high cost of purifying a vaccine in accordance with Food and Drug Administration (FDA) regulations makes oral vaccines prohibitively expensive to produce because they require ten to fifty times more than the regular quantity of vaccine per dose than a vaccine which is parenterally administered. Of all the viral vaccines being produced today only a few are being produced as oral vaccines.

According to FDA guidelines, efficacy of vaccines for humans must be demonstrated in animals by antibody development and by resistance to infection and disease upon challenge with the pathogen. When the safety and immunogenicity levels are satisfactory, FDA clinical studies are then conducted in humans. A small carefully controlled group of volunteers are enlisted from the general population to begin human trials. This begins the long and expensive process of testing which takes years before it can be determined whether the vaccine can be given to the general population. If the trials are successful, the vaccine may then be mass produced and sold to the public.

Even after these precautions are taken, problems can arise. With the killed virus vaccines, there is always a chance that one of the live viruses has survived and vaccination may lead to isolated cases of the disease. Moreover, since both the killed and live attenuated types of virus vaccines are made from viruses grown in animal host cells, the vaccines are sometimes contaminated with cellular material from the animal host which can cause adverse, sometimes fatal, reactions in the vaccine recipient. Legal liability of the vaccine manufacturer for those who are harmed by a rare adverse reaction to a new or improved vaccine necessitates expensive insurance which ultimately adds to the cost of the vaccine.

Some vaccines have other disadvantages. Vaccines prepared from whole killed virus generally stimulate the development of circulating antibodies (IgM, IgG) thereby conferring a limited degree of immunity which usually requires boosting through the administration of additional doses of vaccine at specific time intervals. Live attenuated viral vaccines, while much more effective, have limited shelf-life and storage problems requiring maintaining vaccine refrigeration during delivery to the field.[1]

Efforts today are being made to produce less expensive vaccines which can be administered in a less costly manner. Recombinants or mutants can be produced that serve in place of live virus vaccines. The development of specific deletion mutants that alter the virus, but do not inactivate it, yield vaccines that can replicate but cannot revert to virulence.

Recombinant DNA techniques are being developed to insert the gene coding for the immunizing protein of one virus into the genome of a second, avirulent virus type that can be administered as the vaccine. Recombinant vaccines may be prepared by means of a vector virus such as vaccinia virus or by other methods of gene splicing. Vectors may include not only avirulent viruses but bacteria as well. A live recombinant hepatitis A vaccine has been constructed using attenuated *Salmonella typhimurium* as the delivery vector via oral administration.[1]

Various avirulent viruses have been used as vectors. The gene for hepatitis B surface antigen (HBsAg) has been introduced into a gene non-essential for vaccinia replication. The resulting recombinant virus has elicited an immune response to the hepatitis B virus in test animals. Other virus vectors may possess large genomes, e.g. the herpesvirus. The oral adenovirus vaccine has been modified so that it carries the HBsAg immunizing gene of the hepatitis B virus. Chimeric polio virus vaccines have been constructed of which the completely avirulent type 1 virus acts as a vector for the gene carrying the immunizing VP1 gene of type 3.[1]

Immunity to a pathogenic infection is based on the development of an immune response to specific antigens located on the surface of a pathogenic organism. For enveloped viruses, the important antigens are the surface glycoproteins. Glycosylation of viral surface glycoproteins is not always essential for antigenicity.[1] Unglycosylated herpesvirus proteins synthesized in bacteria have been shown to produce neutralizing antibodies in test animals.[1]

Viral genes which code for a specific surface antigen that produces immunity in humans or animals, can be cloned into plasmids. The cloned DNA can then be expressed in prokaryotic or eukaryotic cells if appropriately engineered constructions are used. The immunizing antigens of hepatitis B virus,[2] foot and mouth,[3] rabies virus, herpes simplex virus, and the influenza virus have been successfully synthesized in bacteria or yeast cells.[1]

Recent advances in genetic engineering have provided the requisite tools to transform plants to contain foreign genes. Plants that contain the transgene in all cells can then be regenerated and can transfer the transgene to their offspring in a Mendelian fashion.[4] Both monocotyledenous and dicotyledenous plants have been stabily transformed. For example, tobacco, potato and tomato plants are but a few of the dicotyledenous plants which have been transformed by cloning a gene which encodes for the expression of 5-enolpyruvyl-shikimate-3-phosphate synthase.[5]

Plant transformation and regeneration in dicotyledons by *Agrobacterium tumefaciens* (*A. tumefaciens*) is well documented. The application of the *Agrobacterium tumefaciens* system with the leaf disc transformation method[6] permits efficient gene transfer, selection and regeneration.

Monocotyledons have also been found to be capable of genetic transformation by *Agrobacterium tumefaciens* as well as by other methods such as direct DNA uptake mediated by PEG (polyethylene glycol), or electroporation. Successful transfer of foreign genes into corn[7] and rice,[8,9] as well as wheat and sorghum protoplasts has been demonstrated. Rice plants have been regenerated from untransformed and transformed protoplasts. New methods such as microinjection and particle bombardment may offer simpler and even more efficient means of transformation and regeneration of monocotyledons.[10]

The present invention overcomes the deficiencies of the prior art by producing oral vaccines in one or more tissues of a transgenic plant, thereby availing large human and animal populations of an inexpensive means of vaccine production and administration. The edible fruit, juice, grain, leaves, tubers, stems, seeds, roots or other plant parts of the vaccine producing transgenic plant is ingested by a human or an animal thus providing a very inexpensive means of immunization against disease. Purification expense and adverse reactions inherent in existent vaccine production are avoided by this invention. These and other aspects of the present invention will become apparent from the following description and drawings.

SUMMARY OF THE INVENTION

The oral vaccine of the present invention is produced in edible transgenic plants and then administered through the consumption of a part of those edible plants. A DNA sequence encoding for the expression of a surface antigen of a pathogen is isolated and ligated into a plasmid vector containing selection markers. A promoter which regulates the production of the surface antigen in the transgenic plant is included in the same plasmid vector upstream from the surface antigen gene to ensure that the surface antigen is expressed in desired tissues of the plant. Preferably, the foreign gene is expressed in a portion of the plant that is edible by humans or animals. For some uses, such as with human infants, it is preferred that the edible food be a juice from the transgenic plant which can be taken orally.

The present invention produces vaccines inexpensively. Further, vaccines from transgenic plants can not only be produced in the increased quantity required for oral vaccines but can be administered orally, thereby also reducing cost. The production of an oral vaccine in edible transgenic plants may avoid much of the time and expense required for FDA approval and regulation relating to the purification of the vaccine.

A principal advantage of the present invention is the humanitarian good which can be achieved through the production of inexpensive oral vaccines which can be used to vaccinate the populations of lesser developed countries who otherwise could not afford expensive oral vaccines manufactured under present methods or vaccines which require parenteral administration.

Other objects and advantages of the invention will appear from the following description.

BRIEF DESCRIPTION OF THE DRAWINGS

For a detailed description of the preferred embodiment of the invention, reference will now be made to the accompanying drawings wherein:

FIG. 1 is a diagrammatic plasmid construct illustrating the construction of the plasmid vector pHVA-1 containing the HBsAg gene for producing the HBsAg antigen in a plant; and FIG. 2 is a map of the coding sequence for two structural genes and their regulatory elements in the plasmid pHVA-1.

DESCRIPTION OF THE PREFERRED EMBODIMENT

The present invention has several components which include: using recombinant DNA techniques to create a plasmid vector which contains a DNA segment encoding one or more antigenic proteins which confer immunity in a human or an animal to a particular disease and for the expression of antigenic protein(s) in desired tissues of a plant; selecting an appropriate host plant to receive the DNA segment encoding antigenic protein(s) and subsequently produce the antigenic protein(s); transferring the DNA segment encoding the antigenic protein(s) from the plasmid vector into the selected host plant; regenerating the transgenic plant thereby producing plants expressing the antigenic protein(s) which functions as a vaccine(s); and administering an edible part of the transgenic plant containing the antigenic protein(s) as an oral vaccine to either a human or an animal by the consumption of a transgenic plant part. The present invention thereby provides for the production of a transgenic plant which when consumed as food, at least in part, by a human or an animal causes an immune response. This response is characterized by resistance to a particular disease or diseases. The response is the result of the production in the transgenic plant of antigenic protein(s). The production of the antigenic protein(s) is the result of stable genetic integration into the transgenic plant of DNA regions designed to cause regulated expression of antigenic protein(s) in the transgenic plants.

Vaccine(s) and Their Administration

The present invention may be used to produce any type vaccine effective in immunizing humans and animals against diseases. Viruses, bacteria, fungi, and parasites that cause disease in humans and animals can contain antigenic protein(s) which can confer immunity in a human or an animal to the causative pathogen. A DNA sequence encoding any of these viral, bacterial, fungal or parasitic antigenic proteins may be used in the present invention.

Mutant and variant forms of the DNA sequences encoding for a antigenic protein which confers immunity to a particular virus, bacteria, fungus or parasite in an animal (including humans) may also be utilized in this invention. For example, expression vectors may contain DNA coding sequences which are altered so as to change one or more amino acid residues in the antigenic protein expressed in the plant, thereby altering the antigenicity of the expressed protein. Expression vectors containing a DNA sequence encoding only a portion of an antigenic protein as either a smaller peptide or as a component of a new chimeric fusion protein are also included in this invention.

The present invention is advantageously used to produce vital vaccines for humans and animals. The following table sets forth a list of vaccines now used for the prevention of viral diseases in humans.

is used as a dietary component while the vaccine is administered in the process.

The present invention allows for the production of not only a single vaccine in an edible plant but for a plurality of vaccines into one foodstuff. DNA sequences of multiple antigenic proteins can be included in the expression vector used for plant transformation, thereby causing the expression of multiple antigenic amino acid sequences in one transgenic plant. Alternatively, a plant may be sequentially or simultaneously transformed with a series of expression vectors, each of which contains DNA segments encoding one or more antigenic proteins. For example, there are five or six different types of influenza, each requiring a different vaccine. A transgenic plant expressing multiple antigenic protein sequences can simultaneously elicit an immune response to more than one of these strains, thereby giving disease immunity even though the most prevalent strain is not known in advance.

Vaccines produced in accordance with the present invention may also be incorporated into the feed of animals. This represents an important means to produce lower cost disease prevention for pets, production animals, and wild species.

Host Plant Selection

A variety of plant species have been genetically transformed with foreign DNA, using several different gene

TABLE

| Disease | Source of vaccine | Condition of virus | Route of Administration |
|---|---|---|---|
| Poliomyelitis | Tissue culture (human diploid cell line, monkey kidney) | Live attenuated Killed | Oral Subcutaneous |
| Measles | Tissue culture (chick embryo) | Live attenuated | Subcutaneous |
| Mumps | Tissue culture (chick embryo) | Live attenuated | Subcutaneous |
| Rubella | Tissue culture (duck embryo, rabbit, or human diploid) | Live attenuated | Subcutaneous |
| Smallpox | Lymph from calf or sheep | Live vaccina | Intradermal |
| Yellow fever | Tissue cultures and eggs | Live attenuated | Subcutaneous |
| Viral hepatitis B | Purified HBsAg from "healthy" carriers Recombinant HBsAg from yeast | Live attenuated Subunit | Subcutaneous Subcutaneous |
| Influenza | Highly purified or subviral forms (chick embryo) | Killed | Subcutaneous |
| Rabies | Human diploid cell cultures | Killed | Subcutaneous |
| Adenoviral infections | Human diploid cell cultures | Live attenuated | Oral |
| Japanese B encephalitis | Tissue culture (hamster kidney) | Killed | Subcutaneous |
| Varicella | Human diploid cell cultures | Live attenuated | Subcutaneous |

The present invention is also advantageously used to produce vaccines for animals. Vaccines are available to immunize pets and production animals. Diseases such as: canine distemper, rabies, canine hepatitis, parvovirus, and feline leukemia may be controlled with proper immunization of pets. Viral vaccines for diseases such as: Newcastle, Rinderpest, hog cholera, blue tongue and foot-mouth can control disease outbreaks in production animal populations, thereby avoiding large economic losses from disease deaths. Prevention of bacterial diseases in production animals such as: brucellosis, fowl cholera, anthrax and black leg through the use of vaccines has existed for many years. Today new recombinant DNA vaccines, e.g. rabies and foot and mouth, have been successfully produced in bacteria and yeast cells and can facilitate the production of a purified vaccine containing only the immunizing antigen. Veterinary vaccines utilizing cloned antigens for protozoans and helminths promise relief from parasitic infections which cripple and kill.

The oral vaccine produced by the present invention is administered by the consumption of the foodstuff which has been produced from the transgenic plant producing the antigenic protein as the vaccine. The edible part of the plant insertive techniques.[10,22-27, 29] Since important progress is being made to clone DNA coding regions for vaccine antigens for parasitic tropical diseases and veterinary parasitic diseases[11-21] the present invention, will have important means of low cost production of vaccines in a form easily used for animal treatment.

Since many edible plants used by humans for food or as components of animal feed are dicotyledenous plants, it is preferred to employ dicotyledons in the present invention, although monocotyledon transformation is also applicable especially in the production of certain grains useful for animal feed.

The host plant selected for genetic transformation preferably has edible tissue in which the antigenic protein, a proteinaceous substance, can be expressed. Thus, the antigenic protein is expressed in a part of the plant, such as the fruit, leaves, stems, seeds, or roots, which may be consumed by a human or an animal for which the vaccine is intended. Although not preferred, a vaccine may be produced in a non-edible plant and administered by one of various other known methods of administering vaccines.

Various other considerations are made in selecting the host plant. It is sometimes preferred that the edible tissue of the host plant not require heating prior to consumption since the heating may reduce the effectiveness of the vaccine for animal or human use. Also, since certain vaccines are most effective when administered in the human or animal infancy period, it is sometimes preferred that the host plant express the antigenic protein which will function as a vaccine in the form of a drinkable liquid.

Plants which are suitable for the practice of the present invention include any dicotyledon and monocotyledon which is edible in part or in whole by a human or an animal such as, but not limited to, carrot, potato, apple, soybean, rice, corn, berries such as strawberries and raspberries, banana and other such edible varieties. It is particularly advantageous in certain disease prevention for human infants to produce a vaccine in a juice for ease of administration to humans such as tomato juice, soy bean milk, carrot juice, or a juice made from a variety of berry types. Other foodstuffs for easy consumption might include dried fruit.

Methods of Gone Transfer into Plants

There are various methods of introducing foreign genes into both monocotyledenous and dicotyledenous plants.[33,34] The principle methods of causing stable integration of exogenous DNA into plant genomic DNA include the following approaches: 1) Agrobacterium-mediated gene transfer;[35,36,37,53] 2) direct DNA uptake,[38] including methods for direct uptake of DNA into protoplasts,[8] DNA uptake induced by brief electric shock of plant cells,[41,42] DNA injection into plant cells or tissues by particle bombardment,[39,44–46] by the use of micropipette systems,[43,47,48] or by the direct incubation of DNA with germinating pollen,[40,49] or 3) the use of plant virus as gone vectors.[33,51]

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation.[6] The Agrobacterium system is especially viable in the creation of transgenic dicotyledenous plants.

As listed above there are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

The last principle method of vector transfer is the transmission of genetic material using modified plant viruses. DNA of interest is integrated into DNA viruses, and these viruses are used to infect plants at wound sites.

In the preferred embodiment of the present invention, the Agrobacterium-Ti plasmid system is utilized.[53] The tumor-inducing (Ti) plasmids of *A. tumefaciens* contain a segment of plasmid DNA called transforming DNA (T-DNA) which is transferred to plant cells where it integrates into the plant host genome. The construction of the transformation vector system has two elements. First, a plasmid vector is constructed which replicates in *Escherichia coli* (*E. coli*). This plasmid contains the DNA encoding the protein of interest (an antigenic protein in this invention); this DNA is flanked by T-DNA border sequences that define the points at which the DNA integrates into the plant genome. Usually a gene encoding a selectable marker (such as a gene encoding resistance to an antibiotic such as Kanamycin) is also inserted between the left border (LB) and right border (RB) sequences; the expression of this gene in transformed plant cells gives a positive selection method to identify those plants or plant cells which have an integrated T-DNA region.[52,53] The second element of the process is to transfer the plasmid from *E. coli* to Agrobacterium. This can be accomplished via a conjugation mating system, or by direct uptake of plasmid DNA by Agrobacterium. For subsequent transfer of the T-DNA to plants, the Agrobacterium strain utilized must contain a set of inducible virulence (vir) genes which are essential for T-DNA transfer to plant cells.[53,54]

Those skilled in the art should recognize that there are multiple choices of Agrobacterium strains and plasmid construction strategies that can be used to optimize genetic transformation of plants. They will also recognize that *A. tumefaciens* may not be the only Agrobacterium strain used. Other Agrobacterium strains such as *A. rhizogenes* might be more suitable in some applications.

Methods of inoculation of the plant tissue vary depending upon the plant species and the Agrobacterium delivery system. A very convenient approach is the leaf disc procedure which can be performed with any tissue explant that provides a good source for initiation of whole plant differentiation. The addition of nurse tissue may be desirable under certain conditions. Other procedures such as the in vitro transformation of regenerating protoplasts with *A. tumefaciens* may be followed to obtain transformed plant cells as well.[33,53]

This invention is not limited to the Agrobacterium-Ti plasmid system but should include any direct physical method of introducing foreign DNA into the plant cells, transmission of genetic material by modified plant viruses, and any other method which would accomplish foreign DNA transfer into the desired plant cells.

Promoters

Once the host plant has been selected and the method of gene transfer into the plant determined, a constitutive, a developmentally regulated, or a tissue specific promoter for the host plant is selected so that the foreign protein is expressed in the desired part(s) of the plant.

Promoters which are known or found to cause transcription of a foreign gene in plant cells can be used in the present invention. Such promoters may be obtained from plants or viruses and include, but are not necessarily limited to: the 35S promoter of cauliflower mosaic virus (CaMV) (as used herein, the phrase "CaMV 35S" promoter includes variations of CaMV 35S promoter, e.g. promoters derived by means of ligations with operator regions, random or controlled mutagenesis, etc.); promoters of seed storage protein genes such as Zma10 Kz or Zmag12 (maize zein and glutelin genes, respectively), light-inducible genes such as ribulose bisphosphate carboxylase small subunit (rbcS), stress induced genes such as alcohol dehydrogenase (Adh1), or "housekeeping genes" that express in all cells (such as Zmaact, a maize actin gene).[4,55] This invention can utilize promoters for genes which are known to give high expression in edible plant parts, such as the potatin gene promoter from potato.[56]

The plasmid constructed for plant transformation also usually contains a selectable or scorable marker gene. Numerous genes for this purpose have been identified.[54,57]

The following is an example of the production of a vaccine for hepatitis B in a host transgenic tomato or tobacco plant and is presented to describe a preferred embodiment and the utility of the present invention but should not be construed as limiting the claims thereof.

EXAMPLE I

The DNA coding sequence for the hepatitis B surface antigen was selected for expression in a transgenic plant.

The tomato and tobacco plants were selected as the host plants to produce the hepatitis B recombinant surface antigen as examples of antigenic protein production in different plant parts.

A. Construction of Hepatitis B Surface Antigen Expression Vector pHVA-1

Referring initially to the diagrammatic plasmid construct illustrated in FIG. 1, the DNA sequence encoding for HBsAg contained within restriction endonuclease sites Pst 1-Hind III on plasmid pWR/HBs-3 was excised and subsequently ligated into the unique Bam H1-Sst 1 site of the excised beta-glucuronidase (GUS) gene on plasmid pB121 to construct the binary vector plasmid pHVA-1.

Plasmid pB121, obtained from Clonetech Laboratories, Inc., Palo Alto, Calif., has cleavage sites for the restriction endonucleases Bam H1 and Sst 1 located between the CaMV 35S promoter and the GUS structural gene initiation sequence and between the GUS gene termination sequence and the NOS polyadenylation signals, respectively. Plasmid pB121 was selected since the GUS structural gene can be excised from the plasmid using Bam H1 and Sst 1, another structural gene encoding an antigenic protein can be inserted, and the new gene will be functionally active in plant gene expression. Plasmid pB121 also contains a NPT II gene encoding neomycin phosphotransferase II; this is an enzyme that confers Kanamycin resistance when expressed in transformed plant cells, thereby allowing the selection of cells and tissues with integrated T-DNA. The NPT II gene is flanked by promoter and polyadenylation sequences from a Nopaline synthase (NOS) gene.

The HBsAg DNA coding sequence[64,65] was isolated from the plasmid pWR/HBs-3 (constructed at the Institute of Cell Biology in China) as a Pst 1-Hind III fragment. This fragment was digested with Klenow enzyme to create blunt ends; the resultant fragment was ligated at the 5' end with Bam H1 linkers and at the 3' end with Sst 1 linkers, and then inserted into the pB121 plasmid at the site where the GUS coding sequence had been excised, thereby creating plasmid pHVA-1 as shown in FIG. 1.

The plasmid vector pHVA-1 then contains 1) a neomycin phosphotransferase II (NPT II) gene which provides the selectable marker for kanamycin resistance; 2) a HBsAg gene regulated by a cauliflower mosaic virus (CaMV 35S) promoter sequence; and 3) right and left T-DNA border sequences which effectively cause the DNA sequences for the NOS and HBsAg genes to be transferred to plant cells and integrated into the plant genome. The diagrammatic structure of pHVA-1 is shown in FIG. 2.

B. Transfer of Binary Vector, pHVA-1, to *A. tumefaciens*

Plasmid pHVA-1, containing the HBsAg gene, was transferred to *A. tumefaciens* strain LBA4404 obtained from Clontech Laboratories, Inc. This strain is widely used since it is "disarmed"; that is, it has intact vir genes, but the T-DNA region has been removed by in vivo deletion techniques. The vir genes work in trans to mediate T-DNA transfer to plants from the plasmid pHVA-1.

*A. tumefaciens* was cultured in AB medium[55] containing two-tenths milligrams per milliliter (0.2 mg/ml) streptomycin until the optical density (O.D.) of the culture reaches about five tenths (0.5). The cells are then centrifuged at 2000 times gravity (2000×G) to obtain a bacterial cell pellet. The Agrobacterium pellet was resuspended in one milliliter of ice cold twenty millimolar calcium chloride (20 mM $CaCl_2$). Five tenths microgram (0.5 μg) of plasmid pHVA-1 DNA was added to two tenths milliliters (0.2 ml) of the calcium chloride suspension of *A. tumefaciens* cells in a one and five tenths milliliter (1.5 ml) microcentrifuge tube and incubated on ice for sixty minutes. The plasmid pHVA-1 DNA and *A. tumefaciens* cells mixture was frozen in liquid nitrogen for one minute, thawed in a twenty-five degree Celsius (25° C.) water bath, and then mixed with five volumes or one milliliter (1 ml) of rich MGL agar medium.[58] The plasmid pHVA-1 and *A. tumefaciens* mixture was then incubated at twenty-five degrees Celsius (25° C.) for four hours with gentle shaking. The mixture was plated on LB, luria broth,[58] agar medium containing two hundred micrograms per milliliter (200 μg/ml) kanamycin. Optimum drug concentration may differ depending upon the Agrobacterium strain in other experiments. The plates were incubated for three days at twenty-five degrees Celsius (25° C.) before selection of resultant colonies which contained the transformed Agrobacterium harboring the pHAV-1 plasmids. These colonies were then transferred to AB media containing two hundred micrograms per milliliter (200 μg/ml) of kanamycin for three days at twenty-five degrees Celsius (25° C.).

The presence of pHVA-1 DNA in the transformed Agrobacterium culture was verified by restriction mapping of the plasmid DNA after alkaline lysis of the bacterial cells.[59]

C. Plant Transformation by *A. tumefaciens* Containing the HBsAg Gene as Part of the Ti Vector System The technique for in vitro transformation of plants by the Agrobacterium-Ti plasmid system is based on cocultivation of plant tissues or cells and the transformed Agrobacterium for about two days with subsequent transfer of plant materials to an appropriate selective medium. The material can be either protoplast, callus or organ tissue, depending upon the plant species. Organ cocultivation with leaf pieces is a convenient method.

Leaf disc transformation was performed in accordance with the procedure of Horsch et al[6]. Tomato and tobacco seedlings were grown in flats under moderate light and temperature and low humidity to produce uniform, healthy plants of ten to forty centimeters in height. New flats were started weekly and older plants were discarded. The healthy, unblemished leaves from the young plants were harvested and sterilized in bleach solution containing ten per cent (10%) household bleach (diluted one to ten from the bottle) nd one tenth per cent (0.1%) Tween 20 or other surfactant for fifteen to twenty minutes with gentle agitation. The leaves were then rinsed three times with sterile water. The leaf discs were then punched with a sterile paper punch or cork borer, or cut into small strips or squares to produce a wounded edge.

Leaf discs were precultured for one to two days upside down on MS104[6] medium to allow initial growth and to eliminate those discs that were damaged during sterilization or handling. Only the leaf discs which showed viability as evidenced by swelling were used for subsequent inoculation. The *A. tumefaciens* containing pHVA-1 which had been grown in AB medium were diluted one to twenty with MSO[6] for tomato inoculation and one to ten for tobacco discs. Leaf discs were inoculated by immersion in the diluted transformed *A. tumefaciens* culture and cocultured on regeneration medium MS 104[6] medium for three days. Leaf discs were then washed with sterile water to remove the free *A. tumefaciens* cells and placed on fresh MS selection medium which contained three hundred micrograms per milliliter (300 μg/ml) of kanamycin to select for transformed plants cells and five hundred micrograms per milliliter (500 μg/ml) carbenicillin to kill any remaining *A. tumefaciens*. The leaf discs were then transferred to fresh MS selection medium at two week intervals. As shoots formed at the edge of the leaf discs and grew large enough for manual manipulation, they were excised (usually at three to six weeks after cocultivation with transformed *A. tumefaciens*) and transferred to a root-inducing medium, e.g. MS rooting medium.[6] As roots appeared the plantlets were either allowed to continue to grow under sterile tissue culture conditions or transferred to soil and allowed to grow in a controlled environment chamber.

D. Selection of Genetically-Engineered Plants Which Express HBsA

Approximately three months (nine months for tomato fruit assays) after the initial cocultivation of the putative HBsAg expressing tomato plants (HB-plants) with *A. tumefaciens*, they were tested for the presence of HBsAg.

1. Biochemical and Immunochemical Assays

Root, stem, leaf and fruit samples of the plants were excised. Each tissue was homogenized in a buffered solution, e.g. one hundred millimolar sodium phosphate (100 mM $Na_3PO_4$), pH 7.4 containing one millimolar ethylenediamine tetraacetate (1.0 mM EDTA) and five-tenths millimolar phenylmethylsulfonyl fluoride (0.5 mMPMSF) as a proteinase inhibitor. The homogenate was centrifuged at five thousand times gravity (5000×G) for ten minutes. A small aliquot of each supernatant was then reserved for protein determination by the Lowry method. The remaining supernatant was used for the determination of the level of HBsAg expression using two standard assays: (a) a HBsAg radioimmunoassay, the reagents for which were purchased from Abbott Laboratories and (b) immunoblotting using a previously described method of Peng and Lam[61] with an anti-HBsAg also purchased from Abbott Laboratories. Depending upon the level of HBsAg expression in each tissue, the supernatant may have been partially purified using a previously described affinity chromatographic method of Pershing et al[62] using commercially available Affi-Gel 10 gel from Bio-Rad Laboratories, Richmond, Calif. The purified supernatant was then concentrated by lyophilization or ultrafiltration prior to radioimmunoassay and immunoblotting.

2. Immunocytochemical Staining

The expression of HBsAg in HB-plants was also determined using immunocytochemistry. Each tissue (root, stem, leaf or fruit) was excised from the HB-plants and fixed overnight at room temperature in a fixative containing four per cent (4%) paraformaldehyde in one hundred millimolar sodium phosphate (100 mM $Na_3PO_4$) buffer, pH 7.3. The HB-plants tissues were then processed for immunoperoxidase and immunofluorescence staining using a standard procedure[61] and an antiHBsAg antibody purchased from Abbott Laboratories. Microscopic sections about ten to fifty micrometers in thickness of HB-plant tissues which express a significant level of HBsAg were readily visualized.

3. Detection of the HBsAg Gene Construct

The stable integration of the HBsAg construct (expression vector) for plant cell transfection was tested by hybridization assays of genomic DNA digested with Eco R1, and with a combined mixture of Bam H1 and Sst 1 in each plant tissue for both controlled and HBsAg-transfected plants with a HBsAg coding sequence probe using standard southern blots[60]. In addition, seeds were collected from self-fertilized plants, and progeny were analyzed by standard Southern analysis.

E. Micropropagation of HBsAg Transgenic Tomato Plants

Once the transgenic plant has been perfected, the transgenic plant is regenerated by growing multiples of the transgenic plant to produce the oral vaccine. Of course, the most common method of plant propagation is by seed. Regeneration by seed propagation, however, has the deficiency that there is a lack of uniformity in the crop. Seeds are produced by plants according to the genetic variances governed by Mendelian rules. Basically, each seed is genetically different and each will grow with its own specific traits. Therefore, it is preferred that the transgenic plant be produced such that the regenerated plant has the identical traits and characteristics of the parent transgenic plant, e.g. a reproduction of the vaccine. Therefore, it is preferred that the transgenic plant be regenerated by micropropagation which provides a rapid, consistent reproduction of the transgenic plants.

Micropropagation is a process of growing new generation plants from a single piece of tissue that has been excised from a selected parent plant or cultivar such as a transgenic HBsAg tomato plant. This process permits the mass reproduction of plants having the preferred tissue expressing the foreign genes for use as vaccines. The new generation plants which are produced are genetically identical to and have all of the characteristics of the transgenic plant. Micropropagation allows mass production of quality plant material in a short period of time and offers a rapid multiplication of selected cultivars in the preservation of the characteristics of the transgenic plant. The advantages of cloning plants are the speed of plant multiplication and the quality and uniformity of plants produced.

Micropropagation is a multi-stage procedure that requires alteration of culture medium or growth conditions between stages. The micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transgenic plantlets are transferred to a greenhouse for hardening where the plants' tolerance to light is gradually increased so that it can be grown in the natural environment.

F. Administration of HBsAg Vaccine to Humans Through Consumption of Tomato Juice Produced from HBsAg Transgenic Tomatoes Once the vaccine is produced through the mass regeneration of the transgenic plant, the crop is harvested and utilized directly as food or processed into a consumable food. Although the food may be processed as a solid or liquid, in some cases it is preferred that it be in liquid form for ease of consumption. The transgenic tomatoes could be homogenized to produce tomato juice which could be bottled for drinking. HBsAg vaccine administration is accomplished by a human drinking the tomato juice or consuming the fruit in a quantity and time scale (once or multiple doses over a period of time) to confer immunity to hepatitis B viruc infection.

The foregoing description of the invention has been directed to a particular preferred embodiment in accordance with the requirements of the patent and statutes and for purposes of explanation and illustration. It will become apparent to those of skilled in the art that modifications and changes may be made without departing from the scope and the spirit of the invention.

The following references are incorporated herein by reference in pertinent part for the reasons cited in the text.

REFERENCES

1. Melnick, J. L., Bul. W.H.O. 67(2), 105–112(1989).

2. Valenzuela, P. et al., *Nature* 298, 347–350(1982).
3. Kupper, H. et al, *Nature* 289, 555–559(1981).
4. Benfey, P. N. and Chua, N. H., *Science* 244, 174–181(1989).
5. Shah, D. M. et al., U.S. Pat. No. 4,940,835 (1990).
6. Horsch, R. B. et al. in *Plant Molecular Biology* Manual A5, Kluwer Academic Publishers, Dordrecht (1988) p. 1–9.
7. Rhodes, C. A. et al., *Science* 240, 204–207 (1989).
8. Toriyama, K. et al., *Bio/Technology* 6, 1072–1074 (1988).
9. Zhang, W. & Wu, R., *Theor. Appl. Genet.* 76, 835–840 (1988).
10. Wu, R. in *Plant Biotechnology*, Kung, S. and Arntzen, C. J., eds., Butterworth Publishers, Boston, Mass. (1989) p. 3551.
11. *Vaccination Strategies of Tropical Diseases*, ed., Liew, F. W., CRC Press, Boca Raton, Fla.; (1989).
12. *New Strategies in Parasitology*, ed., McAdam, K. P. W. J., Churchill Livingstone, New York, N.Y.; (1989).
13. Murray, P. K., Vaccine 7, 291–299 (1989).
14. Weber, J. L. et al., *Exp. Parasitology* 63, 295–300 (1987).
15. Hoffman, S. L. et al., *Science* 252, 520–521 (1991).
16. Khusmith, S. et al., *Science* 252, 715–718 (1991).
17. Kaslow, D. C. et al., *Science* 252, 1310–1313 (1991).
18. Frasch, A. C. E. et al., *Parasitology Today* 7, 148–151 (1991).
19. Mitchell, G. F. et al., *Parasitology Today* 5, 34–37 (1989).
20. Capron, A. et al., *Science* 238 1065–1072 (1987).
21. Lanar, D. et al., *Science* 234, 593–596 (1986).
22. Deak, M. et al., *Plant Cell Rep.* 5, 97–100 (1986).
23. McCormick S. et al., *Plant Cell Rep* 5, 81–84 (1986).
24. Shahin, E. and Simpson, R., *Hort.Sci.* 21, 1199–1201 (1986).
25. Umbeck, P. et al., *Bio/Technology* 5, 263–266 (1987).
26. Christou, P. et al., *Trends Biotechnol.* 8, 145–151 (1990).
27. Datta, S. K. et al., *Bio/Technology* 8, 736–740 (1990).
29. Hinchee, M. A. W. et al., *Bio/technology* 6, 915–922 (1988).
30. Raineri, D. M. et al., *Bio/Technology* 8, 33–38 (1990).
31. Fromm, M. E. et al., *Bio/Technology* 8, 833–839 (1990).
32. Gordon-Kamm, W. J. et al., *The Plant Cell* 2, 603–618 (1990).
33. Potrykus, I., *Annu. Rev. Plant Physiol., Plant Mol. Biol.* 42, 205–225 (1991).
34. Shimamoto, K., et al., *Nature* 338, 274–276 (1989).
35. Klee, H. et al., *Annu. Rev. Plant Physiol.* 38, 467–486 (1987).
36. Klee, H. J. and Rogers, S. G. in *Cell Culture and Somatic Cell Genetics of Plants*, Vol. 6, *Molecular Biology of Plant Nuclear Genes*, eds. Schell, J., and Vasil, L. K., Academic Publishers, San Diego, Calif. (1989) p. 2–25.
37. Gatenby, A. A. in *Plant Biotechnology*, eds. Kung, S. and Arntzen, C. J., Butterworth Publishers, Boston, Mass. (1989) p. 93–112.
38. Paszkowski, J., et al. in *Cell Culture and Somatic Cell Genetics of Plants*, Vol. 6, *Molecular Biology of Plant Nuclear Genes* eds. Schell, J., and Vasil, L. K., Academic Publishers, San Diego, Calif. (1989) p. 52–68.
39. Klein, T. M., et al. in *Progress in Plant Cellular and Molecular Biology*, eds. Nijkamp, H. J. J., Van der Plas, J. H. W., and Van Aartrijk, J., Kluwer Academic Publishers, Dordrecht, (1988) p. 56–66.
40. DeWet, J. M. J., et al. in *Experimental Manipulation of Ovule Tissue*, eds. Chapman, G. P. and Mantell, S. H. and Daniels, W. Longman, London, (1985) p. 197–209.
41. Zhang, H. M. et al., *Plant Cell Rep.* 7, 379–384 (1988).
42. Fromm, M. E. et al., *Nature* 319, 791–793 (1986).
43. Hess, D. *Int. Rev. Cytol.* 107, 367–395 (1987).
44. Klein, T. M. et al., *Bio/Technology* 6, 559–563 (1988).
45. McCabe, D. E. et al., *Bio/Technology* 6, 923–926 (1988).
46. Sanford, J. C., *Physiol. Plant.* 79, 206–209 (1990).
47. Neuhaus G. et al., *Theor. Appl. Genet.* 75, 30–36 (1987).
48. Neuhaus, G. and Spangenberg, G., *Physiol. Plant.* 79, 213–217 (1990).
49. Ohta, Y., *Proc. Natl. Acad. Sci. USA* 83, 715–719 (1986).
51. Fütterer, J., et al., *Physiol. Plant.* 79, 154–157 (1990).
52. Watson, J. D. et al, *Recombinant DNA, a Short Course*, Scientific American Books, dist. W. H. Freeman & Co., New York, N.Y. (1983) p. 164–175.
53. White, F. F. in *Plant Biotechnology*, eds. Kung, S. and Arntzen, C. J., Butterworth Publishers, Boston, Mass. (1989) p. 3–34.
54. Fraley, R. T. in *Plant Biotechnology*, eds. Kung, S. and Arntzen, C. J., Butterworth Publishers, Boston, Mass. (1989), p. 395–407.
55. Elliston, K. and Messing, J. in *Plant Biotechnology*, eds. Kung, S. and Arntzen, C. J., Butterworth Publishers, Boston, Mass. (1989), p. 115–139.
56. Wenzler, H. C. et al., *Plant Mol. Biol.* 12, 41–45 (1989).
57. Weising, K. et al., *Annu. Rev. Genet.* 22, 421–477 (1988).
58. An, G., *Meth. Enzymol.* 153, 292–305 (1987).
59. Maniatis, T., et al., *Molecular Cloning, A Laboratory Manual*, Cold Spring Harbor Laboratory, Cold Spring Harbor, N.Y. (1982), p. 368–369.
60. Chang, A. et al., *Proc. Natl. Acad. Sci., U.S.A.* 86, 9611 (1989).
61. Peng, Y. W. and Lam, D. M. K., *Vis. Neurosci.* 6, 357 (1991).
62. Pershing, D. H. et al., *Proc. Natl. Acad. Sci. U.S.A.* 82, 3440 (1985).
64. Pasek, M. and Goto, T., *Nature* 282, 575–579 (1979).
65. Catlaneo, R., *Nature* 305, 336–338 (1983).

We claim:

1. A plasmid vector for transforming a plant comprising:

a DNA sequence encoding a recombinant hepatitis B viral surface antigen protein; and a plant-functional promoter operably linked to said DNA sequence capable of directing the synthesis of said protein in said plant.

2. The plasmid vector of claim 1 further including a selectable or scorable marker gene.

3. The plasmid vector of claim 1 wherein said plant promoter is a CaMV35S promoter.

4. The plasmid vector of claim 1 wherein said plant is edible.

5. A method for constructing a transgenic tobacco plant cell comprising:

constructing a plasmid vector by operably linking a DNA sequence, said sequence encoding a hepatitis B viral surface antigen protein, to a plant-functional promoter capable of directing the synthesis of said protein in said tobacco plant; and transforming a tobacco plant cell with said plasmid vector.

6. The method of claim 5 further comprising the step of regenerating a transgenic plant from said transgenic plant cell.

7. The method of claim 5 wherein the plasmid vector is a DNA virus.

8. The method of claim 5 wherein the plasmid vector is a binary vector.

9. The method of claim 5 wherein the plasmid vector is an integrative vector.

10. The method of claim 5 wherein the plasmid vector is pB121.

11. The method of claim 5 wherein the plant cell is transformed by microinjection.

12. The method of claim 5 wherein the plant cell is transformed by polyethylene glycol mediated uptake.

13. The method of claim 5 wherein the plant cell is transformed by electroporation.

14. The method of claim 5 wherein the plant cell is transformed by microparticle bombardment.

* * * * *